United States Patent [19]

Parker et al.

[11] Patent Number: 5,443,804
[45] Date of Patent: Aug. 22, 1995

[54] SYSTEM FOR THE MANUFACTURE OF METHANOL AND SIMULTANEOUS ABATEMENT OF EMISSION OF GREENHOUSE GASES

[75] Inventors: Robin Z. Parker, Miami; Robert J. Hanrahan, Gainesville, both of Fla.

[73] Assignee: Solar Reactor Technologies, Inc., Miami, Fla.

[21] Appl. No.: 906,854

[22] Filed: Jun. 30, 1992

Related U.S. Application Data

[63] Continuation-in-part of Ser. No. 526,435, May 22, 1990, Pat. No. 5,219,671, which is a continuation-in-part of Ser. No. 393,814, Aug. 14, 1989, abandoned, which is a continuation of Ser. No. 133,239, Dec. 14, 1987, abandoned, which is a continuation of Ser. No. 804,518, Dec. 4, 1985, abandoned.

[51] Int. Cl.⁶ .................... C01B 31/20; C07C 27/06
[52] U.S. Cl. .................... 423/230; 422/211; 518/713
[58] Field of Search .............. 423/230; 518/713; 422/211

[56] References Cited

U.S. PATENT DOCUMENTS

| | | | |
|---|---|---|---|
| 4,051,005 | 9/1977 | Krascella | 204/157.48 |
| 4,097,348 | 6/1978 | Gomberg | 204/157.48 |
| 4,124,741 | 11/1978 | Hart | 204/129 |
| 4,620,907 | 11/1986 | Gomberg | 204/157.48 |
| 4,725,341 | 2/1988 | Minz | 204/129 |
| 4,937,059 | 6/1990 | Kolts et al. | 423/230 |

OTHER PUBLICATIONS

Spaziante, P. M. et al; Hydrogen/Halogen Energy Storage System: Safety, Performance, and Cost Assessment—Final Report, Feb. 1979; Brookhaven National Laboratory, Upton, New York 11973.
B. Reichman et al., "Photoproduction of Halogens using Platinized $TiO_2$", NA Tech Briefs, (Winter 1980), vol. 5, No. 4, pp. 449, 450.
Chemical Abstracts 115(7):70876g (1991).

*Primary Examiner*—Wayne Langel
*Attorney, Agent, or Firm*—Cushman Darby & Cushman

[57] ABSTRACT

A method for the joint i) abatement of emission of a "greenhouse" gas by removing carbon dioxide from an effluent and ii) manufacture of methanol by reaction of hydrogen with carbon dioxide which includes:
   a) reacting carbon dioxide in the effluent by flowing contact of the effluent with a bed of basic metal oxide at a temperature suitable to form a metal carbonate,
   b) then stopping the effluent flow after said bed has become substantially converted to the carbonate,
   c) heating the carbonate to a temperature suitable to release carbon dioxide,
   d) then mixing the released carbon dioxide with hydrogen while passing the mixture over a catalyst of another metal oxide at a suitable temperature and pressure for a reaction, and thereby forming methanol.

13 Claims, 9 Drawing Sheets

SYSTEM FOR THE MANUFACTURE OF METHANOL AND SIMULTANEOUS ABATEMENT OF EMISSION OF GREENHOUSE GASES

This application is a continuation-in-part of application No. 07/526,435 filed May 22, 1990 now U.S. Pat. No. 5,219,271, issued Jun. 15, 1993, which was in turn a continuation-in-part of application No. 07/393,814 filed Aug. 14, 1989, (abandoned) which was a continuation of application No. 07/133,239, filed Dec. 14, 1987, (abandoned) which was a continuation of application No. 06/804,518 filed Dec. 4, 1985 (abandoned).

BACKGROUND OF THE INVENTION

1. Field of the Invention

The present invention relates generally to an apparatus and method for the manufacture of methanol and the simultaneous abatement of the emission of greenhouse gases.

2. Description of the Related Art

It has been known for many years that the reaction of hydrogen with carbon monoxide over an appropriate catalyst surface leads to the formation of numerous organic compounds: hydrocarbons, alcohols and the like. More recently, it has been found that $H_2+CO_2$ react to produce methanol (purity of 80-90%) with yields of about 1.3% per pass over the catalyst. Much of this work has been performed since 1980.

SUMMARY OF THE INVENTION

It is an object of this invention to provide an improved apparatus and method for generating hydrogen and oxygen from water.

It is an additional object of the present invention to provide an apparatus and method for the solar-augmented electrolytic and thermal production of hydrogen and oxygen.

It is another object of the present invention to provide an apparatus and method for the solar-augmented electrolysis of hydrohalic acid to produce a halogen gas.

It is another object of the present invention to provide an apparatus and method for an integrated, continuously- or intermittently-operable system providing both hydrogen and oxygen generation, and utility load leveling capabilities.

It is another object of the present invention to provide an apparatus and method for both the formation of hydrogen halide, and reformation of hydrohalic acid employed in the electrolysis cell.

It is still another object of the present invention to provide an apparatus and method for the production of potable water from a contaminated water feedstream.

Accordingly, the present invention provides both an apparatus and method for the electrolytic production of hydrogen, and the thermal and photolytic production of oxygen. In the first step of the cycle a concentrated hydrohalic acid solution is electrolyzed to produce hydrogen, halogen, and dilute hydrohalic acid solution. The source of hydrohalic acid can be any source available, hydrogen chloride is preferred. The source of hydrogen chloride (HCl) can be any source available. However, a preferred source would be from a municipal solid waste to energy facility which burns solid waste and produces 3–8 tons of hydrochloric acid (HCl) per 1,000 tons of solid waste from typical municipal waste. Note that the method of this embodiment produces hydrogen and chlorine.

Typical municipal solid waste burning can also be a source of carbon dioxide for another embodiment of this invention, described more fully below, namely the method for abatement of emission of "greenhouse" gas to manufacture methanol by reaction with hydrogen.

Thus, two of the embodiments of this invention could be symbiotic with a municipal solid waste to energy facility, using the HCl and the $CO_2$ from the solid waste to produce methanol for fuel and/or electricity which could be chemically stored during off peak hours for discharge during peak hours.

In the second, or hydrogen halide formation and electrolyte reformation step, the halogen is reacted with steam in a gas phase thermal and photolytic process to reform the hydrogen halide and produce oxygen. An advantage of the novel reformation step is the ability to utilize a contaminated water feedstream for the production of the reusable hydrogen halide.

The present invention also provides both an apparatus and method for the radiation-augmented electrolytic production of hydrogen and oxygen. Reduction of electrical and thermal energy requirements is achieved by using radiation to: (i) activate photosensitive metallic hexahalide ions, which reduces the electrolysis electrode potential; and (ii) energize the hydrogen halide formation reaction. By utilizing radiation-augmented electrolysis, the conventional halogen oxidation reaction is replaced by oxidation of a metallic hexahalide, which occurs at a lower overvoltage and smaller reversible cell potential. Radiant energy thus both replaces electrical energy for the production of hydrogen, and increases the efficiency of electrical energy storage.

Another embodiment of this invention is a method for the joint i) abatement of emission of a "greenhouse" gas, by removing carbon dioxide from an effluent from burning fossil fuel or other source of carbon dioxide and ii) manufacture of methanol by reaction of hydrogen with carbon dioxide. The fossil fuel could be coal or any petroleum product, typically fuel oil. The method comprises a) reacting carbon dioxide in the effluent of the burning of fossil fuel or other source of carbon dioxide such as from fermentation, from a municipal waste treatment facility or from a lime kiln, by flowing contact of the effluent with a bed of basic metal oxide at a temperature suitable to form a metal carbonate, b) then stopping the effluent flow after the bed is substantially converted to the carbonate, and c) heating the carbonate to a temperature suitable to release carbon dioxide, then d) mixing the released carbon dioxide with the hydrogen, e) while passing the mixture over the catalyst of another metal oxide at a suitable temperature and pressure for a reaction, thereby f) forming methanol. Preferably the method temperature of step a) is from about 330° to about 380° C. and the pressure is atmospheric. Preferably the temperature of step c) is from about 475° to about 550° C. and the pressure is atmospheric. Preferably the temperature of step e) is from about 140° to about 310° C. and the pressure is from about 5 to about 55 atmospheres. Although any source can be used, the preferred source of hydrogen in step d) is from a radiation augmented electrolytic production process. Also, preferably there are a plurality of beds of metal oxide of step a) and at least one of the beds is used to react with carbon dioxide as in step a) to form carbonate while the other bed is being heated as in step c) to release carbon dioxide. In a more preferred embodiment, the temperature of step a) is from about 350° C. to about 375° C. and the pressure of step a) is atmospheric, the temperature of step c) is from about 500° to about 540° C., the pressure of step c) is atmospheric, the temperature of step e) is from about 150° to about 300° C. and the pressure of step e) is from about 10 to about 50 atmospheres.

The preferred metal oxide for step a) is selected from the group consisting of magnesium oxide, calcium oxide, zinc oxide and mixtures thereof. The preferred metal oxide catalyst of step c) is selected from the group consisting of ZnO on $ZrO_2$, CuO on ZnO, CuO/ZnO/$Al_2O_3$ and mixtures thereof.

Another embodiment of this invention is the apparatus for the joint i) abatement of emission of a "greenhouse" gas carbon dioxide from burning fossil fuel or other source of carbon dioxide such as from fermentation, from a municipal waste treatment facility or from a lime kiln and ii) manufacture of methanol by reaction of hydrogen and carbon dioxide. The apparatus comprises a) means for reacting carbon dioxide in the effluent of a burning fossil fuel or other source of carbon dioxide such as from fermentation, from a municipal waste treatment facility or from a lime kiln by flowing contact of effluent with a bed of basic metal oxide to form a metal carbonate, b) means for stopping effluent flow after the bed is substantially converted to the carbonate, c) means for heating carbonate to a temperature suitable to release carbon dioxide, d) means for mixing the released carbon dioxide with the hydrogen, e) means for passing the mixture over a catalyst of another metal oxide to thereby form methanol. The preferred means for reacting in means a) is a bed of metal oxide mounted in the effluent conduit from a burning fossil fuel. The preferred means for stopping the effluent in means b) is a damper in the conduit. It is also preferred that there be a plurality of the beds mounted in a plurality of conduits. Then these beds are alternately i) used to react carbon dioxide with the metal oxide then ii) heated to release carbon dioxide by means of alternately opening and closing a damper system in the conduit. The preferred means of heating c) is a system to pass heated inert gas across the carbonate. The preferred means of passing the mixture over a catalyst is a reactor system, which can be a fixed bed, a mixed bed, or a fluidized bed.

BRIEF DESCRIPTION OF THE DRAWINGS

Other objects, features, and advantages of the present invention will become more fully apparent from the following detailed description of the preferred embodiments, the appended claims, and the accompanying drawings. As depicted in the attached drawings:

DESCRIPTION OF THE PREFERRED EMBODIMENTS

Figure 1A:
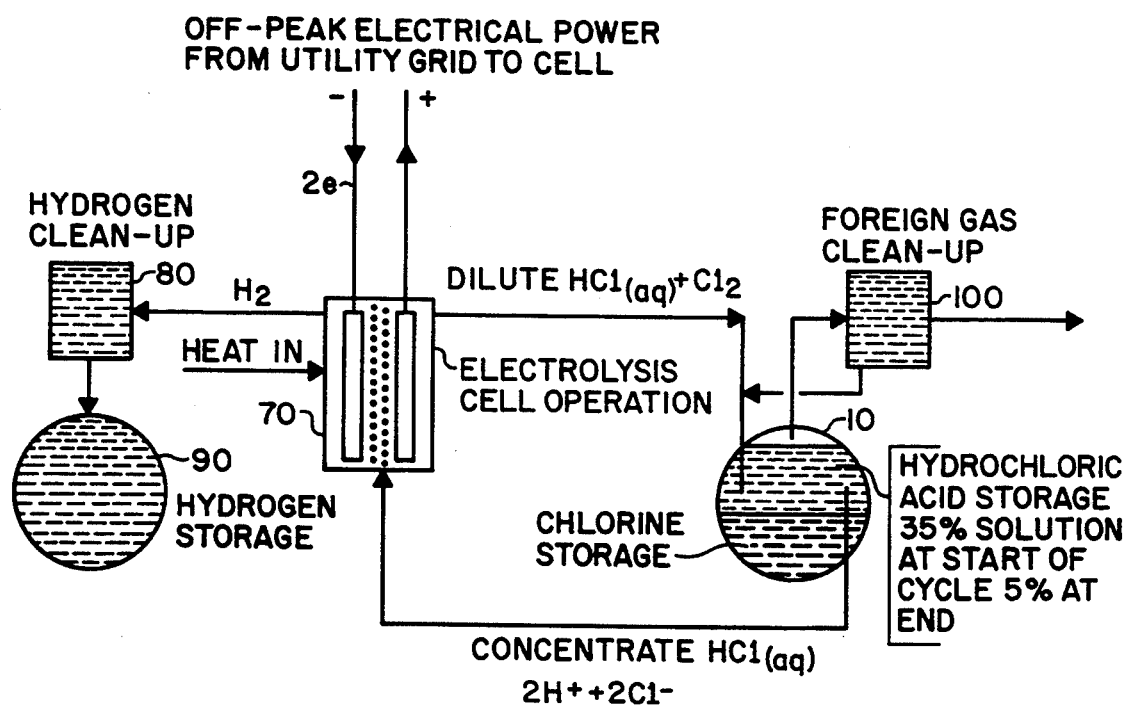
FIGS. 1A and 1B are schematic block diagram of the apparatus and method embodied by a conventional hydrogen-halogen load leveling battery.
Figure 1B:
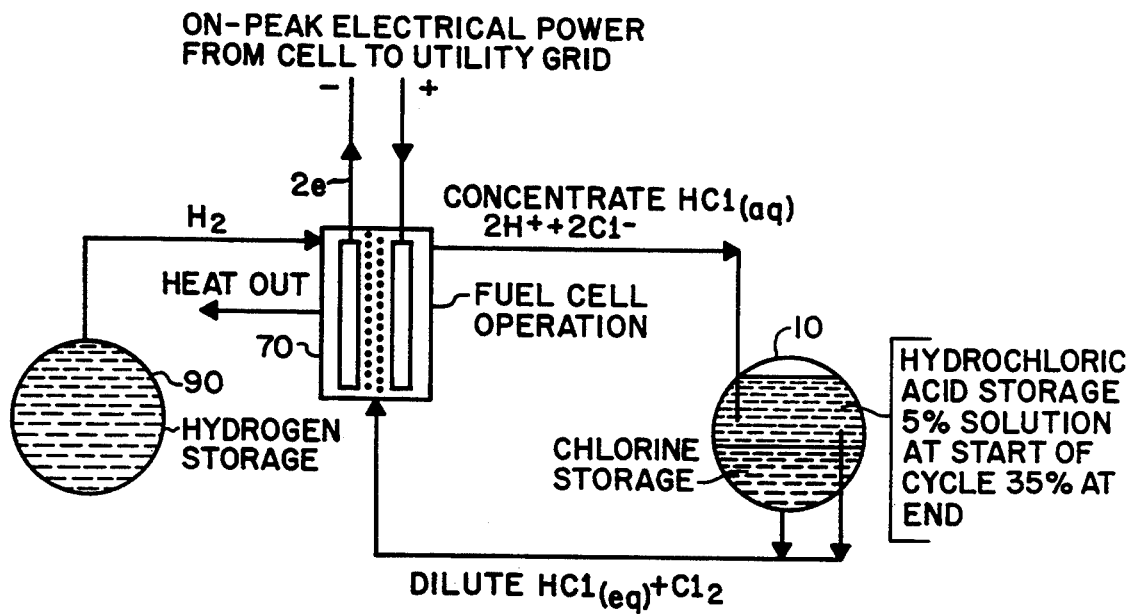

The present invention will be disclosed in terms of the currently perceived preferred embodiments thereof.

By way of example, the present invention will be disclosed in connection with Group VIII transition metals, halogens, and halide ions. For illustrative purposes, iridium is disclosed as the transition metal, and chlorine as the halogen component.

The radiation flux employed may generally be described as electromagnetic radiation. Preferably, that other sources of radiation energy might be suitably employed. Exemplary alternative sources include photons generated from nuclear-excited flash lamps, alpha particles, beta particles, gamma rays, x-rays, protons, or fission fragments.

The present invention facilitates use of different combinations of solar, thermal, and electrical power in an integrated system for hydrogen production and/or utility load leveling.

A fundamental basis of the first embodiment of the present invention lies in the fact that the voltage required to electrolyze a hydrochloric acid solution is less than that required to electrolyze water. In the electrolysis of hydrochloric acid, hydrogen is liberated at the cathode and chlorine is liberated at the anode, whereas in the electrolysis of water, hydrogen is liberated at the cathode and oxygen is liberated at the anode. Furthermore, both the E° value for the chlorine half cell and the overpotential of chlorine are lower than that for oxygen. Additionally, as a result of the temperature dependence of the E° value, increased ion mobility at high temperature leading to decreased IR drop, and diminished overvoltage, the voltage required to electrolyze HCl decreases with an increase in temperature.

The water-chlorine cycle employed in the first illustrative embodiment uses electrical, thermal, and photolytic energy to convert water to hydrogen and oxygen as marketable products. The process reverses the hydrogen combustion reaction (1) in two steps, using chlorine as an intermediate which is not consumed. The reactions and their enthalpies at 298 K are:

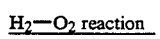

-continued $$H_2 + \tfrac{1}{2} O_2 \longrightarrow H_2O \quad -15.11 \text{ kw-hr/lb } H_2 \quad (1)$$

H$_2$—Cl$_2$ reaction $$H_2 + Cl_2 \longrightarrow 2HCl \quad -11.54 \text{ kw-hr/lb } H_2 \quad (2)$$

Electrolyte reformation reaction $$H_2O + Cl_2 \longrightarrow 2HCl + \tfrac{1}{2} O_2 \quad 3.57 \text{ kw-hr/lb } H_2 \quad (3)$$

HCl electrolysis $$2HCl \longrightarrow H_2 + Cl_2 \quad 11.54 \text{ kw-hr/lb } H_2 \quad (4)$$

Reaction (4), the major energy-consuming step, uses electrical power to electrolyze the HCl formed by Reaction (3). The cost of producing hydrogen by electrolysis is proportional to the voltage of the electrolysis cell.

In the first step of the hydrogen production (or battery charging) cycle, a concentrated hydrochloric acid solution is electrolyzed to produce hydrogen, chlorine, and dilute hydrochloric acid solution. In the second, or hydrogen halide formation and electrolyte reformation step, the chlorine is reacted with steam in a gas phase thermal process to form hydrogen chloride and oxygen, and then solvated.

Figure 2:
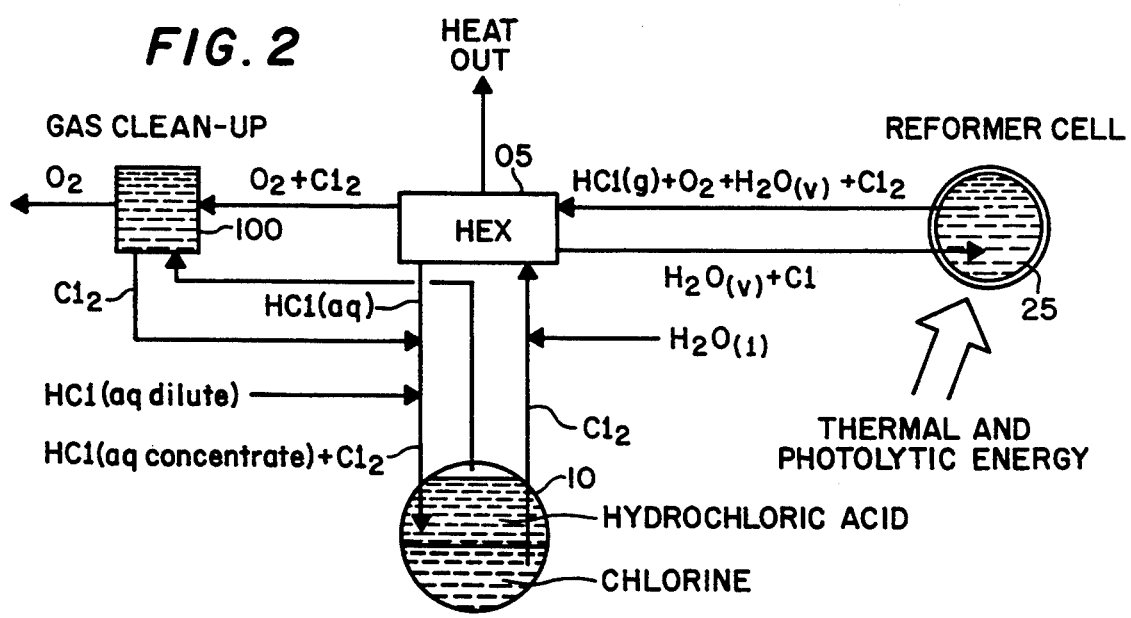
FIG. 2 is a schematic block diagram of the apparatus and method embodied by the hydrogen halide formation, and electrolyte reformation, modes of operation of the present invention.

The apparatus and method of an illustrative embodiment of the invention will now be described with reference to FIG. 2. In the hydrogen halide formation mode of operation, chlorine from acid and chlorine storage vessel 10 and liquid water are conveyed to heat exchange apparatus 05 for preheating. The gaseous chlorine and water are then further heated in reformer cell 25 by means of both thermal and photolytic energy, where they react to produce hydrogen chloride and oxygen, with equilibrium amounts of steam and chlorine.

In the electrolyte reformation mode of operation, the aforementioned hydrogen chloride, oxygen, steam, and chlorine are then cooled in heat exchange apparatus 05, where the condensed water acts to solvate the hydrogen chloride to dilute hydrochloric acid. Gaseous oxygen and chlorine are vented and conveyed to gas cleanup unit 100.

The hydrogen halide formation process has been examined in detail and found to be feasible at 600° C. and to occur with good yields and without undesired byproducts At 600° C. an HCl yield of 79.9% and an O$_2$ yield of 79.3% were achieved.

The oxygen produced during the formation step can he separated from the chlorine using any suitable conventional separation technique. Exemplary techniques include separation based on boiling points, in which the mixture is cooled to −40° C. to liquefy the chlorine while oxygen remains in the gaseous phase; membrane separation; differential adsorption; and flow separation, based on the solubility of chlorine in a solution of hydrochloric acid.

In the flow technique, a mixture of chlorine and oxygen is passed through a solution of hydrochloric acid flowing downward. The solubility of Cl$_2$ increases in an HCl solution, due to the formation of Cl$_3^-$:

$$Cl_2 + Cl^- \rightarrow Cl_3^-$$

Oxygen will move in the upward direction, thus separating the two gases. In the reformation of HCl from chlorine and steam, if chlorine is used as a limiting reactant, only a small amount of unreacted chlorine will be present with a large quantity of oxygen.

In a variation of the first illustrative embodiment, the invention produces hydrogen while operating as a load leveling battery by charging and discharging at different current densities. By maintaining the voltage at a nearly constant value, but increasing the current density substantially on charging, the rate and amount of hydrogen produced increases. Though the power consumed during charging will increase as a result of the increased current density, it is lower-cost, off-peak power. Optionally, the same effect could be attained by charging for a longer period of time than the time of discharge.

Of the increased amount of hydrogen produced during the charging cycle, a portion is utilized in the fuel cell discharge mode, and the balance is available for export as a product. The additional hydrochloric acid required for the surplus hydrogen production is attained through electrolyte reformation from the chlorine produced during the battery charging cycle.

In an additional illustrative embodiment of the present invention, an apparatus and method for the solar-augmented electrolytic and thermal production of hydrogen and oxygen are provided. Reduction of electrical and thermal energy requirements is achieved by using solar energy to: (i) activate photo-sensitive metallic hexahalide ions, which reduces the electrolysis electrode potential; and (ii) energize a portion of the hydrogen halide reformation reaction. By utilizing solar-augmented electrolysis, the conventional halogen oxidation reaction is replaced by oxidation of the metallic hexahalide, which occurs at a lower overvoltage and smaller reversible cell potential. Solar energy thus replaces both electrical power and thermal energy to eliminate a significant portion of the cost of either hydrogen production or electrical energy storage.

The present invention describes a method for both hydrogen production and electrical energy storage by utilizing a combination of electrolysis, photolysis, and electrolyte reformation. The electrolysis process is based on the electrochemistry of a hydrohalic acid electrolyte. The photolytic process is based on the photochemistry of transition metal complex ions.

The aqueous hydrohalic electrolyte contains another electrolyte, consisting of a metallic element of the type known as a Group VIII transition or post-transition element, along with a suitable counter-ion of opposite charge. The metallic element will be in a positive oxidation state. The overall charge of the complex ion, e.g., a metallic hexahalide $ZX_6$, where Z is the transition metal and $X_6$ is the hexahalide, could be minus three (−3), or $ZX_6^{-3}$.

Under the influence of an electric field, the negative ion $ZX_6^{-3}$ migrates toward the anode, where it is oxidized, leading to an ion of minus two (−2) charge:

$$ZX_6^{-3} \rightarrow ZX_6^{-2} + e^-.$$

The species $ZX_6^{-2}$ is then exposed to visible light, whereby it is promoted to an excited electronic state:

$$ZX_6^{-2} + h\nu \rightarrow (ZX_6^{-2})^*.$$

The $(ZX_6^{-2})^*$ is then able to oxidize the halide ion in a hydrohalic acid, for example, which has a minus one (−1) oxidation state, to the elemental halogen, which has a zero oxidation state:

$$(ZX_6^{-2})^* + X^- \rightarrow ZX_6^{-3} + \tfrac{1}{2}X_2$$

To ensure that the process proceeds as desired, it is required that the $ZX_6^{-2}$ absorb visible light more strongly than the $ZX_6^{-3}$. This condition can be achieved by providing these species in the form of the indicated complex ions. These species consist of a central Group VIII metallic ion in the positive oxidation state, surrounded and bound to one or more charged or neutral ions or molecules referred to as ligands.

Exemplary metallic ion species include Fe, Co, Ni, Ru, Rh, Pd, Os, Ir, and Pt. Typical oxidation states of these ions may range from $+1$ to $+8$. Typical ligands include molecules such as $H_2O$, $NH_3$, and CO, as well as ions such as $CN^-$, $NO_2^-$, $Cl^-$, $Br^-$, and $I^-$.

An example of the photochemical effect of transition metal complex ions is the charge transfer transition in $IrCl_6^{-3}$ when subjected to radiation at visible wavelengths. This reaction is described by H. B. Gray, *Science*, Vol. 214 (1981), 1201:

$$IrCl_6^{-2} + Cl^- + h\nu \rightarrow IrCl_6^{-3} + \tfrac{1}{2}Cl_2 \quad (5)$$

In principle, a related charge transfer transition in $IrCl_6^{-3}$ could facilitate the reduction of protons, completing a cycle that produces hydrogen and chlorine from HCl and water:

$$IrCl_6^{-3} + H^+ + h\nu \rightarrow IrCl_6^{-2} + \tfrac{1}{2}H_2 \quad (6)$$

Since the absorption coefficient of $IrCl_6^{-2}$ is more than an order of magnitude smaller than that of $IrCl_6^{-2}$ at solar wavelengths, however, the quantum yield for the formation of $H_2$ is small. Reaction (6) is therefore not feasibly integrated in a practical cycle.

A high quality aspect of solar radiation is the short average wavelength of solar photons of approximately 500 nm. The energy of an average solar photon is sufficient to cause selected photochemical reactions which can produce energy which may then be stored for subsequent use. Photochemical research has demonstrated that when HCl solutions containing $IrCl_6^{-2}$ ions are irradiated, $IrCl_6^{-3}$ and chlorine gas are produced. The lower overvoltage and smaller reversible cell potential associated with the anodoic oxidation of $IrCl_6^{-3}$ is the basis for employing solar energy to reduce the cost of producing electrolytic hydrogen and oxygen.

Solar-augmented electrolysis thus comprises supplying an aqueous solution of HCl and $IrCl_6^{-2}$ to a photolysis cell, which is irradiated to reduce the $IrCl_6^{-2}$ to $IrCl_6^{-3}$ and produce gaseous $Cl_2$, which is continuously swept from the cell. The aqueous solution of HCl and $IrCl_6^{-2}$ is then introduced into an anode half cell which is separated from the cathode half cell by a semipermeable membrane. An electrical potential is applied across the anode and the cathode, whereby $IrCl_6^{-3}$ is oxidized to $IrCl_6^{-2}$ at the anode, and $H_2$ is evolved at the cathode.

Of the two redox reactions (5) and (6), reaction (5) is spontaneous in the presence of sunlight and reaction (6) is not. In an embodiment of the present invention, the redox reactions are therefor organized such that the photolysis reaction in a separate photocell may be combined with conventional electrolysis.

Conventional electrolysis of HCl(aq) consists of the following half reactions:

$$2H^+ + 2e^- \rightarrow H_2(gas) \quad \text{Cathode} \quad (7)$$

$$2Cl^- \rightarrow Cl_2(gas) + 2e^- \quad \text{Anode} \quad (8)$$

In the process according to the present invention, reaction (7) is unchanged. The anode reaction is replaced with a cycle including the photochemical redox reaction (5) and an electrolysis half-cell reaction. The mechanism of the solar-augmented anode reaction is as follows:

$$IrCl_6^{-2} + h\nu \rightarrow IrCl_6^{-2+} \quad (9)$$

$$IrCl_6^{-2+} + Cl^- \rightarrow IrCl_6^{-3} + \tfrac{1}{2}Cl_2 \quad (10)$$

$$IrCl_6^{-3} \rightarrow IrCl_6^{-2} + e^- \quad (11)$$

Reaction (9) is the photo excitation step; reaction (10) represents the electron transfer from the chloride ion to the excited iridium chloride; and, reaction (11) represents the donation of an electron by $IrCl_6^{-3}$. The overall reaction may thus be generically represented as:

$$aq\ H^+ + Cl^- + h\nu + e^- \xrightarrow{cat} \tfrac{1}{2}H_2 + Cl_2 \quad (12)$$

Reaction (12) thus illustrates the overall photolysis and electrolysis of hydrochloric acid in an aqueous solution seeded with iridium hexachloride. The catalyst is aqueous $IrCl_6^{-2}/IrCl_6^{-3}$.

Though the photolysis step has been described in terms of the use of a single species of metallic hexahalide, other embodiments thereof are possible. To supplement the individual absorption spectrum and thereby provide a broader band and more continuous absorption of photolytic energy, more than one type of metallic hexahalide may be used simultaneously. Thus, exemplary multi-metallic hexahalide solutions could include $RuCl_6/RhCl_6/IrCl_6$, or any suitable combination of the Group VIII metals in conjunction with a single halogen species. The metallic hexahalides selected are those with a half-cell potential for oxidation which is lower than that of the halogen gas alone, to ensure that the gas is not evolved at the anode.

Figure 3:
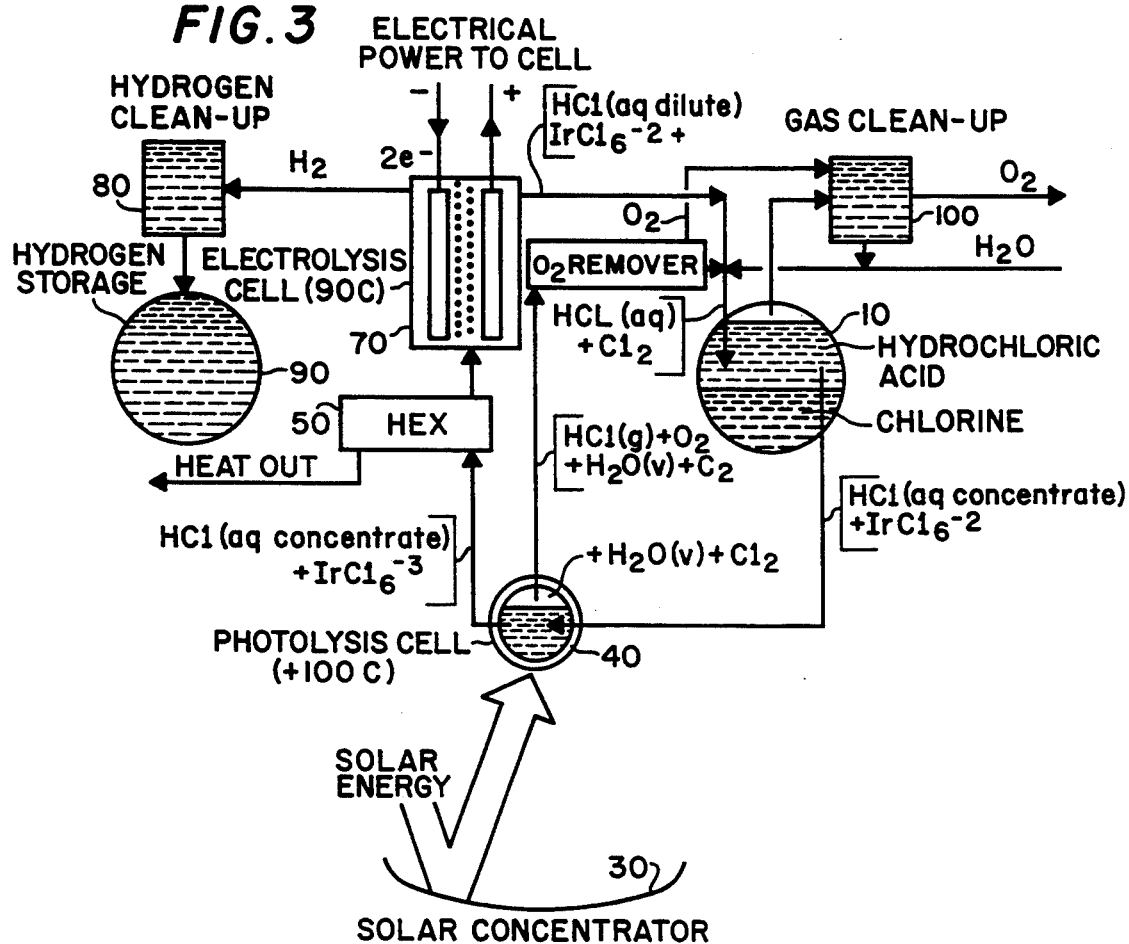
FIG. 3 is a schematic block diagram of the apparatus and method preferably embodied by the radiation-augmented, hydrogen-halogen battery for the production of hydrogen and oxygen.

The apparatus and method of an additional illustrative embodiment will now be described with reference to FIG. 3. In the solar-augmented mode of operation, a concentrated aqueous solution of HCl and $IrCl_6^{-2}$ is conveyed from acid and chlorine storage vessel 10 to photolysis cell 40. Solar radiation is introduced into the photolysis cell by means of solar concentrator 30. To ensure that the photolytic reaction proceeds, the chlorine evolved must be swept from the photolytic solution and conducted away from the cell. Exemplary methods of effecting the chlorine sweep are based on partial pressure reduction, and include steam stripping or boiling with an inert gas. The chlorine conducted from the photolysis cell is utilized to produce HCl by means of the electrolyte reformation process. The $IrCl_6^{-3}$ produced in the photolysis step is conducted to the anode chamber of electrolysis cell 70.

Since the operating temperature of the photolysis cell is preferably above 100° C. and that of the electrolysis cell is below 90° C., means are provided for further enhancing the thermal efficiency of the process by recovering heat from the $IrCl_6^{-3}$/HCl stream through a conventional heat exchange apparatus 50. The anode chamber of the electrolysis cell is separated from the cathode chamber by a semipermeable membrane.

Means are provided for applying an electrical potential across the anode and cathode cells.

Gaseous hydrogen evolved in the cathode cell is conveyed to hydrogen clean-up unit 80 for the removal of impurities, and introduced to hydrogen storage vessel 90. $IrCl_6^{-2}$ evolved in the anode cell and the dilute aqueous solution of HCl are conveyed to acid and chlorine storage vessel 10. Oxygen gas produced during the hydrogen halide formation process is withdrawn and delivered to foreign gas clean-up unit 100 for removal of impurities.

Figure 4:
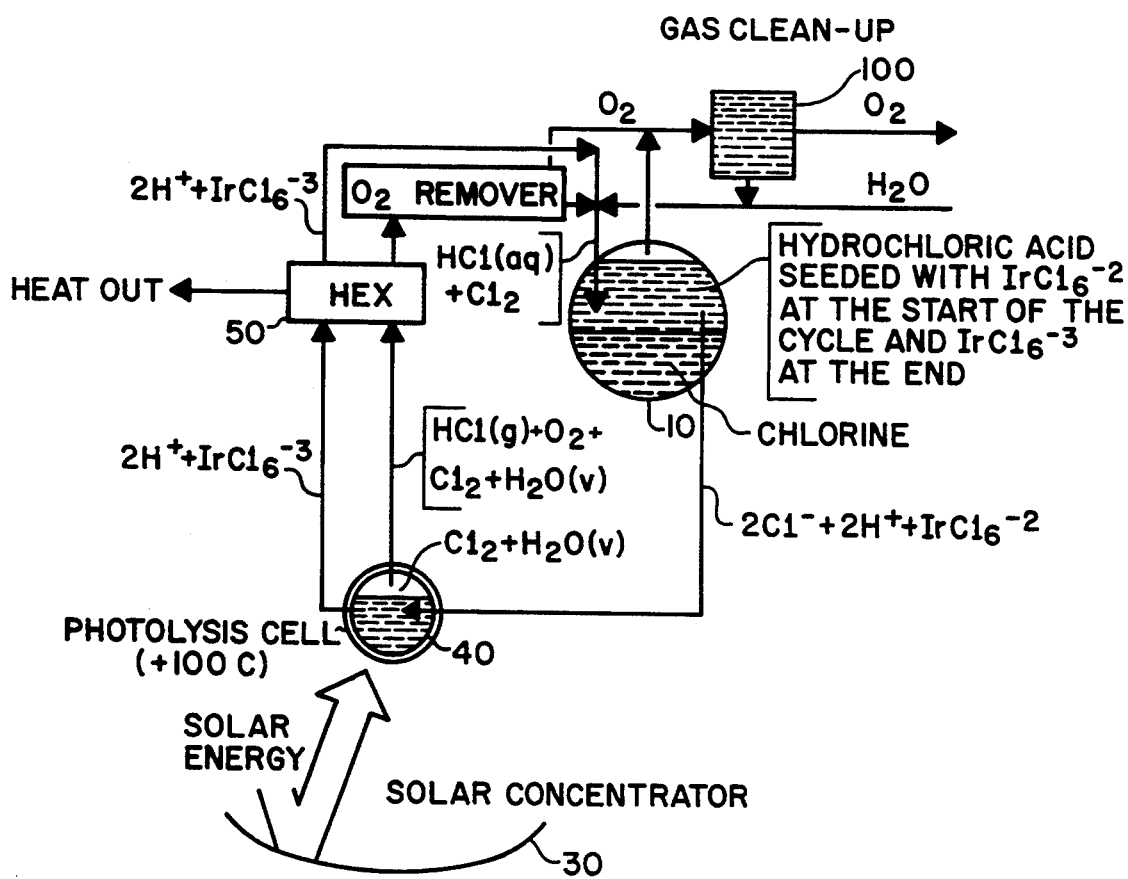
FIG. 4 is a schematic block diagram of the apparatus and method preferably embodied by the electrolyte-conditioning and -storage mode of operation of the present invention.

The apparatus and method of another illustrative embodiment will now be described with reference to FIG. 4, which depicts the electrolyte-conditioning and—storage mode of operation of the present invention. During the solar day, a hydrochloric acid solution seeded with $IrCl_6^{-2}$ at the start of the cycle is photolyzed to establish an inventory of $IrCl_6^{-3}$. The $IrCl_6^{-3}$ is then stored for subsequent electrolysis during periods of off-peak power.

In the electrolyte-conditioning mode of operation, an aqueous solution of HCl and $IrCl_6^{-2}$ is conveyed from acid and chlorine storage vessel 10 to photolysis cell 40. Solar radiation is introduced into the photolysis cell by means of solar concentrator 30. Chlorine evolved in the photolysis step is conducted away from the photolysis cell, and is reformed to HCl by means of the electrolyte reformation process The $IrCl_6^{-3}$ produced in the photolysis step is then cooled in heat exchanger 50 and returned to acid and chlorine storage vessel 10.

Figure 5:
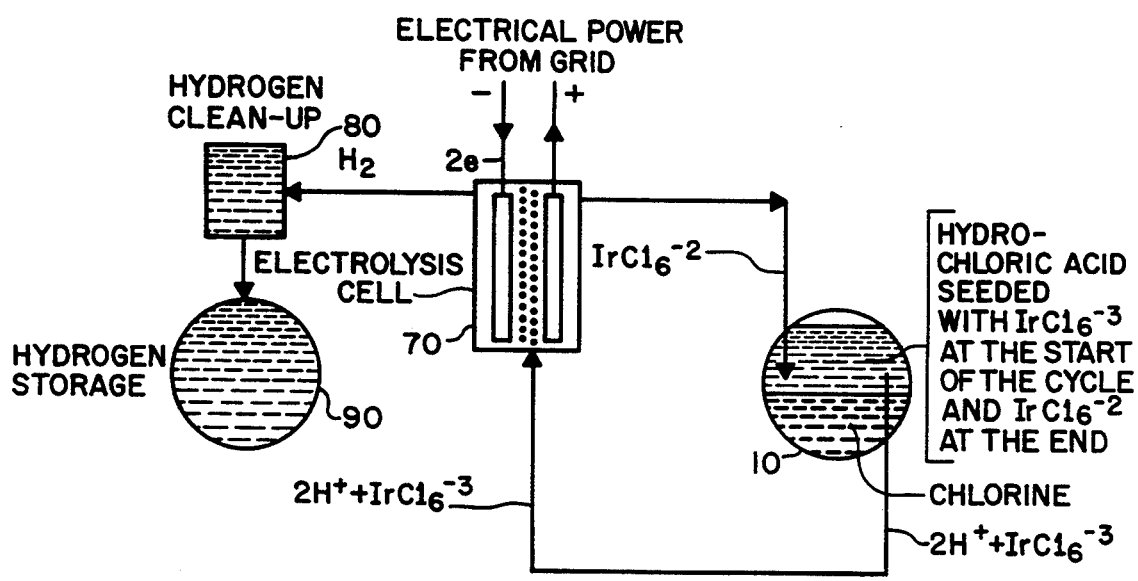
FIG. 5 is a schematic block diagram of the apparatus and method preferably embodied by the charging of the radiation-augmented battery mode of operation of the present invention.

The apparatus and method of another illustrative embodiment will now be described with reference to FIG. 5, which depicts the charging of the radiation-augmented battery mode of operation of the present invention. This embodiment utilizes the pre-conditioned inventory of $IrCl_6^{-3}$ generated during the solar day for the electrolytic production of hydrogen during periods of off-peak power.

In the radiation-augmented battery mode of operation, an aqueous solution of HCl and $IrCl_6^{-3}$ is conveyed from acid and chlorine storage vessel 10 to electrolysis cell 70. Gaseous hydrogen evolved in the cathode cell is conveyed to hydrogen clean-up unit 80 for the removal of impurities, and introduced to hydrogen storage vessel 90. $IrCl_6^{-2}$ evolved in the anode cell and the aqueous solution of HCl are conveyed to acid and chlorine storage vessel 10.

Figure 6:
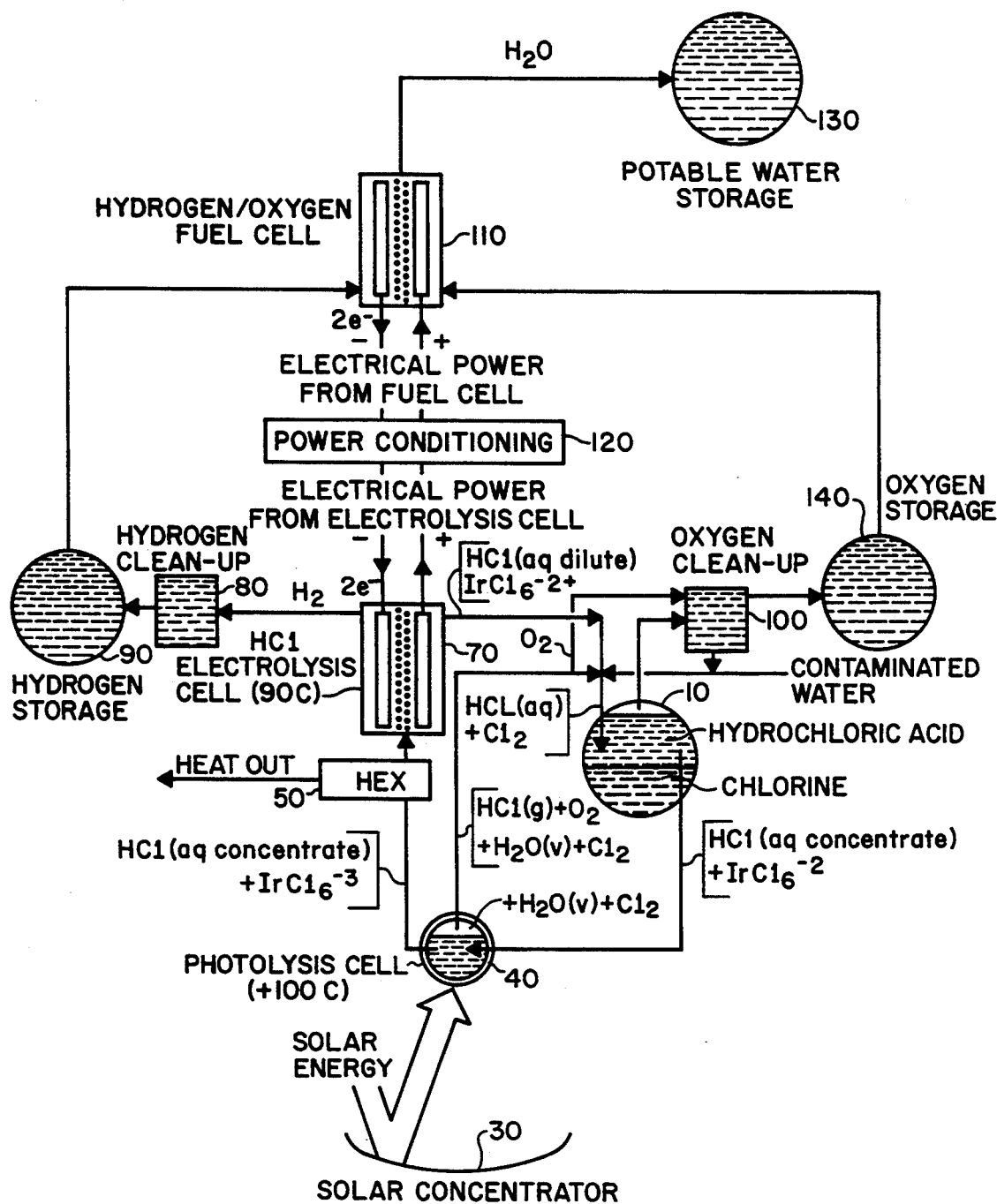
FIG. 6 is a schematic block diagram of the apparatus and method preferably embodied by the potable water production mode of the present invention.

The apparatus and method of another illustrative embodiment will now be described with reference to FIG. 6, which depicts the potable water production mode of the present invention. This embodiment represents an integrated system for the production of potable water from the hydrogen and oxygen generated during solar-augmented electrolysis.

A contaminated water feedstream may be utilized in the process for reformation of the hydrogen chloride. Hydrogen produced during solar-augmented electrolysis, and oxygen produced during the reformation step, are combined in fuel cell 110 to generate electrical power and potable water. The electrical power is conducted to power conditioning unit 120 for subsequent use in electrolysis cell 70.

In another embodiment, this invention simultaneously addresses two problems.

(1) The United States, and other countries as well, seem to be approaching an era when energy sources in general, and liquid fuels in particular, will be in short supply.

(2) The unabated release of greenhouse gases, especially $CO_2$, into the atmosphere is attributed to a warming of the climate of the Earth.

This invention is a method and apparatus which attacks both of the above problems simultaneously. The essence of the approach is to regard the $CO_2$ content of smokestack effluent from fossil fuel burning power plants, or from other industrial facilities burning large amounts of coal, oil, natural gas, etc., not as an obvious and necessary potential environmental disaster, but rather as a source of recoverable energy via capture and recycling of the $CO_2$ content.

It is proposed to capture the $CO_2$ contents from any source such as a power plant, municipal waste treatment or other stack gas trains, fermentation or lime kiln effluent using basic metal oxides such an MgO, CdO, CaO, ZnO or possibly others such as $Sc_2O_3$, BeO, $La_2O_3$, $Co_2O_3$ or NiO. These oxides will react with $CO_2$ to form carbonates such as $ZnCO_3$, $CdCo_3$, $CaCO_3$, $MgCO_3$, etc.

Hydroxides such as $Mg(OH)_2$, $Zn(OH)_2$, $Cd(OH)_2$, $Ca(OH)_2$, etc. can also form, and account must be taken of this possibility. Fortuitously, in several cases the temperature at which $H_2O$ is released from the hydroxide is lower than the temperature at which $CO_2$ is released from the carbonate. For example, in the case of MgO, magnesium hydroxide decomposes (at one atmosphere) at 268° C., whereas, $MgCO_3$ decomposes at 402° C. (Lange's Handbook, 13th Ed.) Accordingly, by maintaining a bed of MgO at approximately 350° to 375° C. it is possible to selectively remove $CO_2$ from a flow gas containing both $H_2O$ and $CO_2$ admixed with about 80% $N_2$ at a total pressure of 1 atm, forming $MgCO_2$ and leaving water vapor in the flowing gas train. Other references give different and somewhat conflicting data on the temperatures of melting and decomposition of $Mg(OH)_2$ and $MgCO_3$, but in all cases it is reported that the vapor of $H_2O$ over $Mg(OH)_2$ reaches a given pressure (for example, 1 atm) at a temperature almost 200 degrees centigrade below that at which the vapor of $CO_2$ over $MgCO_2$ reaches that pressure.

It is proposed to operate an apparatus as described above for a period of time until nearly the entire bed of metal oxide has been converted to carbonate. Then, for example by opening and closing appropriate dampers, flues or valves, the temperature of the bed can be increased to near 540° C., and all of the $CO_2$ driven out essentially as one slug. This gas is then admixed with hydrogen, and flowed over an appropriate catalytic substrate to form $CH_3OH$. In practical application, it would be desirable to have two metal oxide beds such that one is absorbing $CO_2$ while the second bed is eluting previously trapped $CO_2$.

As another embodiment, it is useful to use solar energy as the heat energy source for the steps involving the release of $CO_2$ from the solid carbonate, and/or for the solar augmented reaction converting $CO_2$ plus $H_2$ into $CH_3OH$. The process may be operated with or without the solar aspect. Profitable operation of a system as described may depend on the following factors:

(1) In principle, a large amount of methanol could be produced—the carbon content of the input fuel could be converted almost stoichiometrically into methanol. Therefore, the entire facility would best be designed as a "co-generation facility", optimized simultaneously the generation of energy and production of methyl alcohol.

(2) If the whole procedure is to be feasible, a ready source of non-fossil $H_2$ is required. This could be obtained, for instance, by electrolysis of water produced using solar or nuclear energy. In particular, it would be advantageous to use hydrogen gas produced by the process disclosed in U.S. Pat. No. 5,219,671, further identified above.

(3) It is entirely possible that in the near future, power plants or other large users of fossil fuel will be charged an "environmental impact" fee depending on the mass of $CO_2$ released to the atmosphere. Since no $CO_2$ would be released at the site of the co-generation facility, the net saving on the impact fee would in effect be a credit towards the plant operation.

(4) It will be seen that, overall, a given quantity of carbon (say one mole) would be burned twice—once in the form of coal, fuel oil, etc., at the power plant site, releasing energy and forming the by-product methanol, $CH_2OH$. The same mass of carbon would be burned again, typically in a vehicle as an automobile or aircraft, which would presumable release $CO_2$ to the atmosphere. Overall, however, the net release of $CO_2$ into the atmosphere would in effect be halved.

(5) Since methanol is a clean burning fuel, having no disadvantageous environmental aspects other than the release of $CO_2$, it is entirely possible that a facility could be operated with production of methanol as the primary purpose; in that case, electrical energy (or in some circumstances process steam) is regarded as a by-product.

(6) It is clear that other gases such as $SO_2$, $H_2S$, and $NO_x$ would exist in a power plant stack gas along with the relatively benign water and the desirable $CO_2$. It is expected that corresponding useful materials could ultimately be produced as by-products, including elemental sulfur, sulfuric acid, nitric acid, etc. Sale of such products would justify the added expense of separating and processing such materials.

(7) In many existing facilities, the final temperature of the stack gas prior to release to the atmosphere might be too low to operate the metal oxide, (e.g., MgO, CaO, etc.) absorption beds. A proposed solution is to locate the adsorption bed intermediate between the furnace and the steam boiler. It should be possible to design an apparatus in such a way that the heat is primarily directed to the boiler as desired, while simultaneously producing the metal carbonate.

(8) It will be noted that the two stages of the $CO_2$ entrapment process involve reactions which are the reverse of each other.

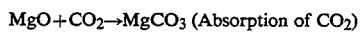

$MgO + CO_2 \rightarrow MgCO_3$ (Absorption of $CO_2$)

$MgCO_3 \rightarrow MgO + CO_2$ (Release of $CO_2$)

The two values of the enthalpy change would be exactly equal in magnitude but opposite in sign at a fixed temperature, and should differ only moderately over, say, 200° C. temperature differential. (The Gibbs free energy changes sign due to the favorable entropy change of releasing $CO_2$ gas.) Thus, if heat energy from absorption of $CO_2$ by the metal oxide $MO_2$ is retained for use in other parts of the process (desorbing the $CO_2$ from the second absorber bed, providing process steam, pre-warming the combustion air stream, etc.) the net energy requirement of trapping $CO_2$ should be small. Conservation of the heat released could be accomplished by use of known technology such as countercurrent heat flow or heat pipes.

The implementation of the $CO_2$ desorption cycle described above uses hot stack gas from the furnace for elution of trapped $CO_2$ from the exhausted metal oxide bed. This gas is expected to consist mainly of $N_2$, $CO_2$, and water vapor, since most of the oxygen will have been consumed to support combustion of the fuel. An alternate design of the $CO_2$ desorption apparatus and operating method is proposed, in which an inert gas such as $N_2$ is heated by a heat exchanger placed in contact with the hot furnace gases, either before or after the main boiler tubes.

Figure 7:
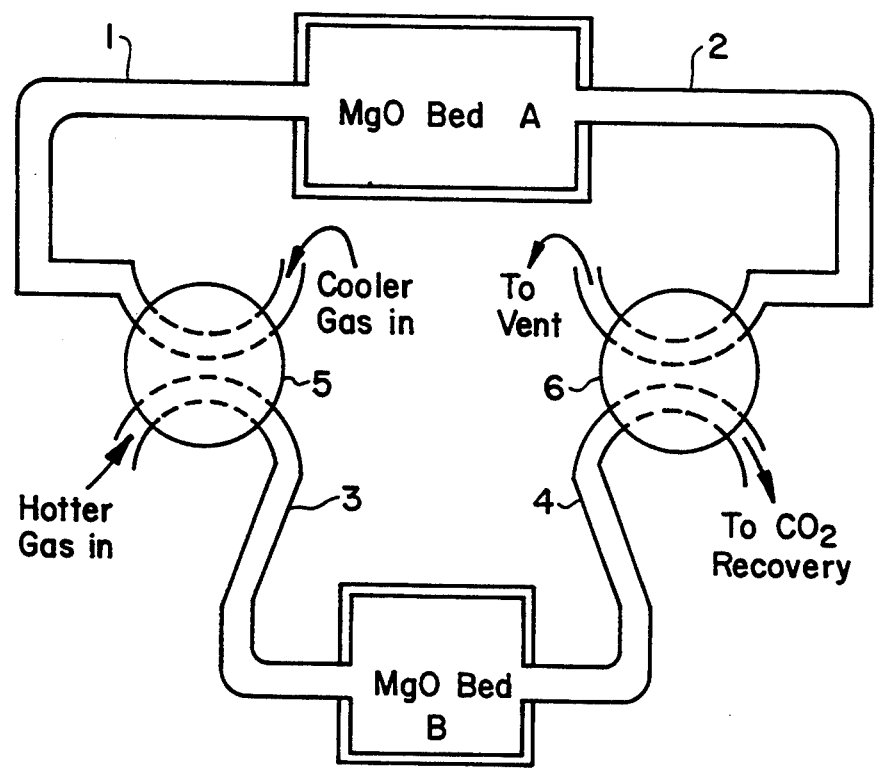
FIG. 7 and 7A are schematic diagrams of the apparatus and method embodied by the $CO_2$ deposition mode followed by the $CO_2$ release mode of the present invention, using two bed of metal oxide, alternately.
Figure 7A:
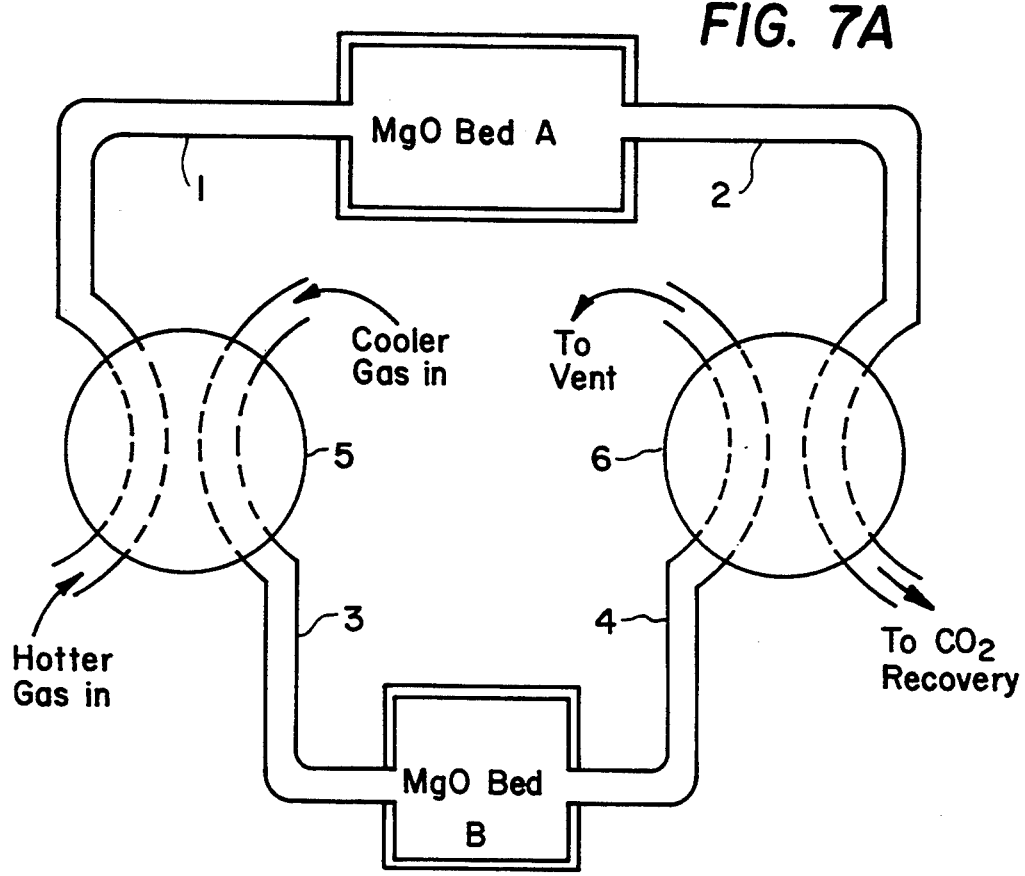

The flow of the two gas streams, that is either the hot $N_2$ or the $CO_2$—rich furnace gas, is diverted as desired between the two metal oxide $CO_2$-entrapment beds by dampers or valving as in FIGS. 7 and 7A.

Figure 9:
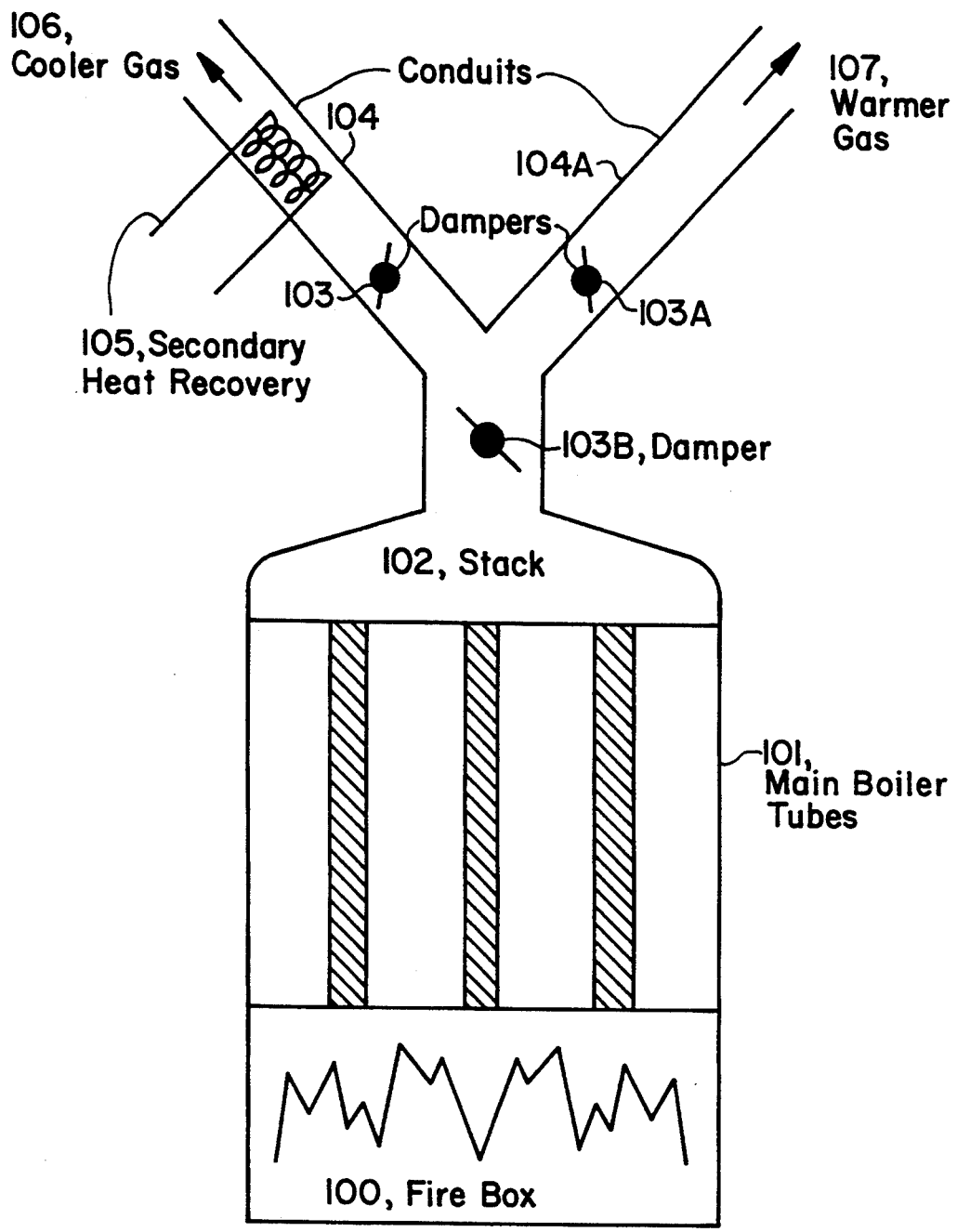
FIG. 9 is a schematic diagram of a fired heater apparatus associated with the generation of $CO_2$ in an effluent for this invention.

In FIG. 7 bed A is reacting with carbon dioxide to form magnesium carbonate in bed A by effluent gas coming in as the cooler gas through line 1 which after having carbon dioxide removed passes to vent to line 2. Simultaneously, bed B is being heated by hot gas coming through line 3 to drive off carbon dioxide through line 4. The reverse arrangement is shown in FIG. 7A wherein bed B is receiving the cooler gas containing carbon dioxide to line 3 to form the carbonate and the gas is removed to vent through line 4 while simultaneously the hotter gas is introduced to bed A through line 1 and carbon dioxide is driven off through line 2. This is achieved by simply switching the dampers or valves 5 and 6 as shown in the two alternative positions in FIGS. 7 and 7A. The source of the carbon dioxide fossil fuel can be as shown in FIG. 9 wherein a fossil fuel is burned in firebox 100 and the effluent gases pass through main boiler tubes 101 to stack 102 which has conduits 104 and 104a splitting therefrom. Dampers 103,103a and 103b are used to control the flow of gases. Secondary heat recovery 105 is used in conduit 104 to form cooler gas 106 whereas no heat recovery is used in conduit 104a and warmer gas 107 results.

PRODUCTION OF METHANOL

Carbon dioxide separated from furnace gas as described above can be hydrogenated over one of several catalysts to produce methanol plus water, using one of several known procedures. The hydrogen and carbon dioxide are delivered separately to the reactor system via valving and flow control apparatus. Since water is a product of the reaction, it is desired to have the feed mixture as water-free as possible, to avoid a le Chatelier shift back towards reactants. The reactor system can be fabricated according to any of several standard designs, including fixed-bed, mixed-bed, or fluidized bed designs. Several catalyst systems are known for efficient conversion of carbon dioxide and hydrogen into methanol plus water, according to the reaction:

$CO_2 + 3 H \rightarrow CH_2OH + H_2O$

Systems which have been described include ZnO on ZrO, CuO on ZnO, and $CuO/ZnO/AlO_3$, also generally described as a Cu—Zn—Al catalyst. For use the catalysts are typically exposed to the $H_2$ and $CO_2$ mixture at 300–500 degrees C., and moderate pressures of one to several atmospheres. This treatment tends to reduce metal oxides to metals, which are present during actual use of the catalysts. The synthesis reaction itself is appropriately carried on at temperatures in the range of 150° C. to 250°-300° C. Higher temperatures are neither appropriate nor required, since the equilibrium in the reaction of $CO_2$ and $H_2$ to make methanol and water becomes increasingly unfavorable as temperature increases above ambient. Since in the reaction four moles of gas yields two moles, a moderate increase in pressure can be advantageous. Moderate pressures in the range of 10 to 50 atmospheres are adequate for the process. Hydrogen can readily be recovered and recycled; it is advantageous to use an excess of hydrogen compared to $CO_2$ pressure, greater than the 3:1 value based on reaction stoichiometry.

A preferred embodiment and best mode of this part of the overall process consists of 10 weight % of ZnO on ZrO support; temperature 360° C.; $CO_2/H_2$ ratio 1:3; total pressure of 10 atm; and a gas flow rate of 6.5 millimole per hour per gram of catalyst. This procedure converts the reactants to methanol of more than 99% purity with an efficiency of approximately 1.3% per pass over the catalyst. Admixture of CuO with the ZnO, and use of $AlO_3$ support in lieu of ZrO have also been described but it is not obvious that better results were obtained.

For the primary purpose of the manufacture of methyl alcohol, set forth in this disclosure, catalysts as described above, consisting generally of moderately active metals such as copper, zinc, and aluminum, are effective.

However, it is known that mixtures of $CO_2$ plus $H_2$ can be catalytically reacted to give hydrocarbon gases, in preference to methanol, over somewhat more active catalyst such as those including the metals cobalt, palladium, and platinum. Under some commercial circumstances, it is possible that coproduction of hydrogen gases plus processes steam (or other forms of available energy) might have more value than production of methanol. It is accordingly possible to suggest an alternate embodiment in which hydrocarbon gases are produced rather than methanol.

The effluent from the reactor bed, consisting of a mixture of water and methanol in the gas phase, with residues of $CO_2$ and/or $H_2$, is cooled in order to condense out the liquid water and methanol as a homogeneous mixture. Residual $H_2$ and $CO_2$ is recirculated for use in the process. Methanol (b.p. 65° C.) and water (b.p. 100° C.) are separated by distillation. An advantage of the overall system as described is the availability of inexpensive or waste heat from the system consisting of the furnace/boilers/flues and heat exchange units. This heat can be advantageously used to provide the reaction temperature for the methanol synthesis and to provide the heat required for the distillation of water-methyl alcohol mixture. In practice, the apparatus shown in the figure for condensation of the methanol-water mixture can be designed so as to constitute both condensation and distillation in one unit, so that water is withdrawn as a liquid at temperature below 100° C., and methanol is obtained as a vapor which is condensed at temperatures below 65° C., and the $H_2$—$CO_2$ excess gas returned to the reactor bed as described previously.

Figure 8:
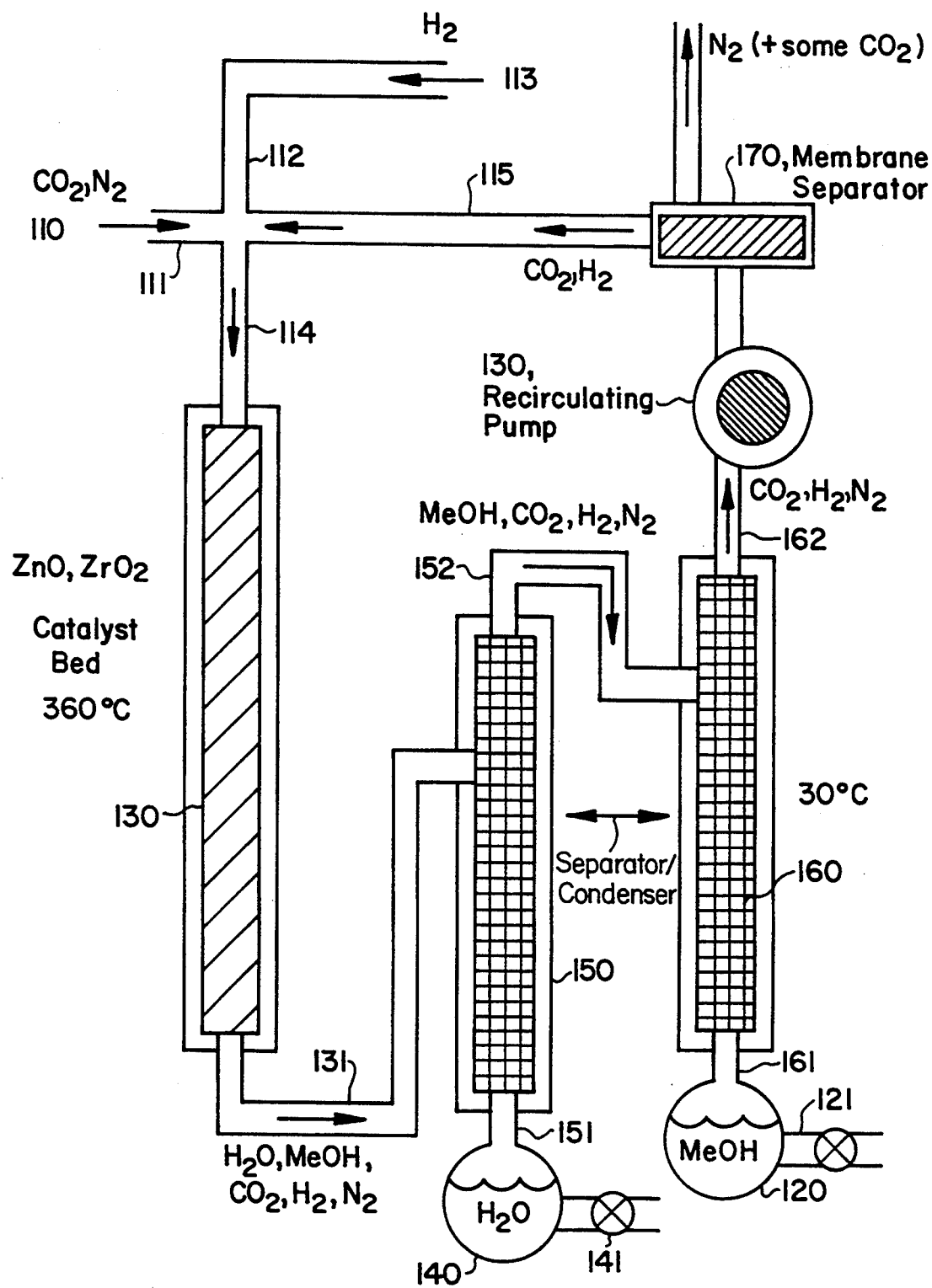
FIG. 8 is a schematic diagram of the apparatus and method embodied by a methanol manufacture embodiment of operation of the present invention.

A typical apparatus to prepare methanol is shown in FIG. 8. The carbon dioxide which may contain inert nitrogen is received from source 110 which may be, for example, the $CO_2$ recovery lines 2 or 4 in FIGS. 7 and 7A. Gas flows through line 111 and joins fresh hydrogen make up gas from source 113 through line 112 along with carbon dioxide hydrogen and nitrogen recycle coming from line 115 as shown. These three effluents join in line 114 to flow across catalyst bed 130. This catalyst is a zinc oxide, zirconium oxide catalyst operating at about 360° C. The effluent from catalyst bed 130 exits through line 131 and contains water, methanol, carbon dioxide, hydrogen and nitrogen which then enters separator/condenser 150 which is held at 80° C. at the bottom and 50° C. at the top, thereby separating out the water through line 151 into container 140 where water is removed through line 141. Gases from separator 150 flow overhead through line 152 and contain carbon dioxide, hydrogen and methanol. Then the methanol is separated out with condenser 160 containing inert packing maintained at about 30° C. The methanol exits through line 161 into container 120 and is removed through methanol removal line 121. The overhead gas goes through line 161 and contains carbon dioxide, hydrogen and nitrogen for recycle which is fed to recirculating pump 130 which has for its outlet line 115.

In order to prevent accumulation of excess $N_2$ in the system, a membrane gas separator (known in the art and commercially available) is installed in line 115, following recirculating pump 130. Nitrogen (along with some $CO_2$ as a result of imperfect separation) is vented to atmosphere, while nearly all of the $H_2$ and much of the $CO_2$ is recycled. (Loss of some $CO_2$ is tolerated to facilitate operation of the membrane separator. $H_2/N_2$ separation is fast and efficient but good $CO_2/N_2$ separation is more difficult; loss of some $CO_2$ is not a problem.) Pump 130 is required to maintain at least a 3:1 pressure drop across the membrane separator in order to drive the separation process.

Figure 10:
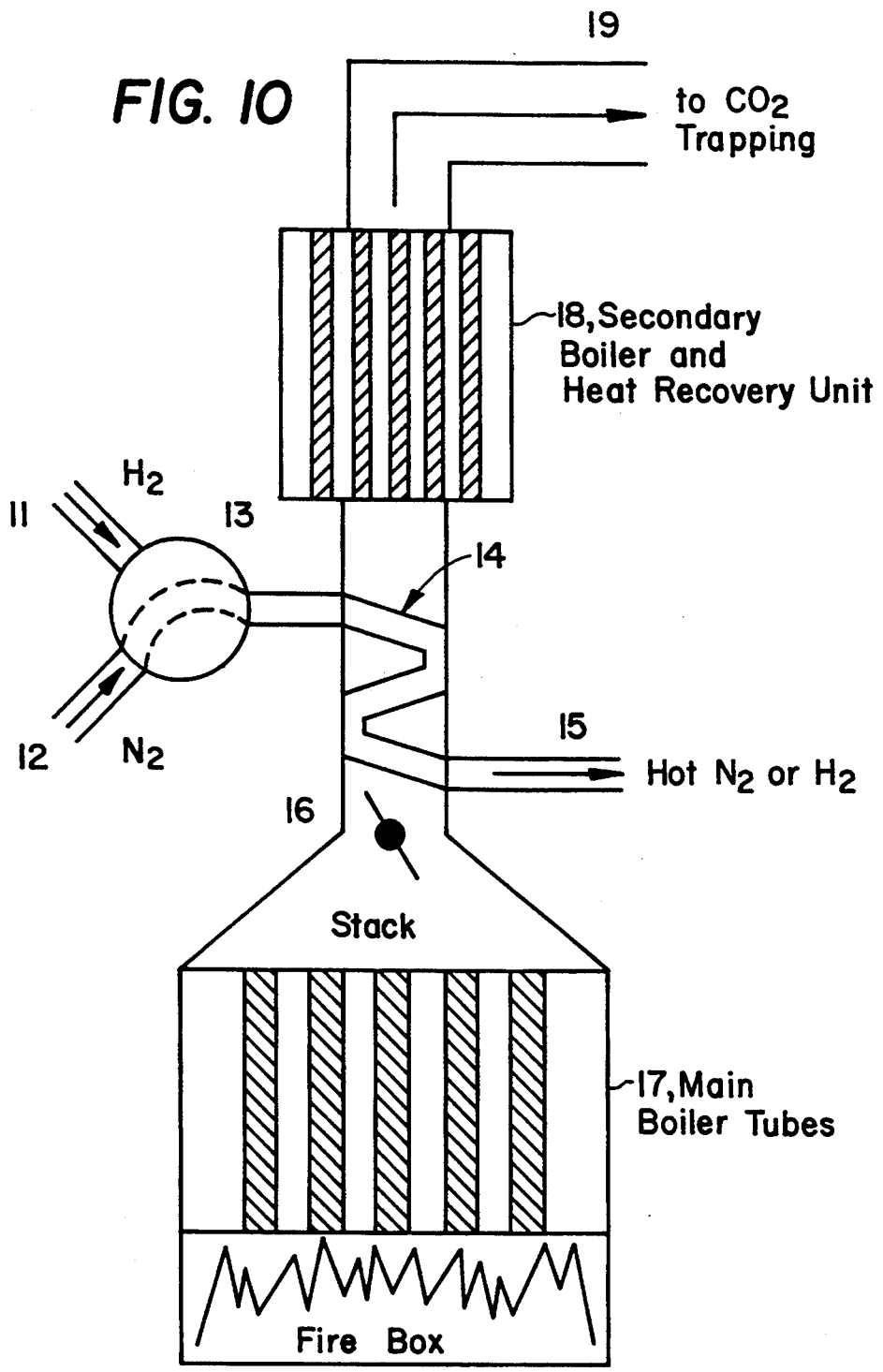
FIG. 10 is a schematic diagram of a fired heater apparatus showing another embodiment useful to heat the $N_2$ or $H_2$ purge gas for use in the apparatus to produce methanol, such as in FIG. 8.

A further embodiment of the invention uses hot hydrogen gas to elute $CO_2$ from the metal oxide beds shown in FIG. 7. This embodiment requires a different version of the furnace/boiler arrangement, as shown in FIG. 10. In this case, the flue above the primary boiler tubes 17 includes a heat exchange coil 14 which is used to heat gases for desorbing $CO_2$ from the trapping beds. Using valve 13, either an inert gas (preferably $N_2$) introduced from pipe 11, or $H_2$ introduced from pipe 12, is heated with coil 14 and then directed the switching valve 15 of FIG. 17. This gas flow (either $N_2$ or $H_2$) is adjusted to be approximately 200° C. hotter than the flue gas from which $CO_2$ is recovered. Combustion gases flow through stack 16 across coil 14 and secondary heat recovery unit 18 and through pipe 19 for $CO_2$ recovery.

As valves 5 and 6 of FIG. 7B are switched to begin eluting $CO_2$ from MgO bed B, the gas flow line 5 from the apparatus in FIG. 10 at first contains inert $N_2$ gas, which flows over bed B of FIG. 7, warming it. During this stage, the output gas from bed B of FIG. 7, carried via line 4 through valve 6, is harmlessly vented to air, since it contains nearly pure nitrogen gas. During this same time, the gases contained in the methanol producing apparatus of FIG. 8 continue to recycle under influence of pump 130, with no input through line 110 for that period. Since the gas mixture on average needs to flow across the catalyst bed about 75 times for complete conversion to methanol, temporary intermittent interruption of input of fresh $CO_2$ into the apparatus of FIG. 8 is acceptable.

When the MgO bed B of FIG. 7B is almost hot enough to start releasing $CO_2$, the gas carried by tube 15 of FIG. 10 is switched over to pure $H_2$, using valve 3 of FIG. 10. Also at that time, the output gas in pipe 4 of FIG. 7B is directed input line 110 of FIG. 8. In this embodiment, input line 110 of FIG. 8 conveys a mixture of $CO_2$ and $H_2$ gases; no nitrogen is present. This embodiment has an important advantage, since the membrane separator 130 of FIG. 8 is not required, and is eliminated. As a result, pump 130 operates with a lower power requirement, since the pressure differential needed for membrane separation is avoided.

For the primary purpose of the manufacture of methyl alcohol (methanol), set forth in this embodiment, catalysts as described above, consisting generally of moderately active metals such as copper, zinc, and aluminum, are effective.

However, it is known that mixtures of $CO_2$ plus $H_2$ can be catalytically reacted to give hydrocarbon gases, in preference to methanol, over somewhat more active catalyst such as those including the metals cobalt, palladium, and platinum. Under some commercial circumstances, it is possible that coproduction of hydrogen gases plus processes steam (or other forms of available energy) might have more value than production of methanol. It is accordingly possible to suggest an alternate embodiment in which hydrocarbon gases are produced, rather than methanol.

The effluent from the reactor bed, consisting of a mixture of water and methanol in the gas phase, with residues of $CO_2$ and/or $H_2$, is cooled in order to condense out the liquid water and methanol as a homogeneous mixture. Residual $H_2$ and $CO_2$ are recirculated for use in the process. Methanol (b.p. 65° C.) and water (b.p. 100° C.) are separated by distillation. An advantage of the overall system as described is the availability of inexpensive or waste heat from the system consisting of the furnace/boilers/flues and heat exchange units. This heat can be advantageously used to provide the reaction temperature for the methanol synthesis and to provide the heat required for the distillation of the water-methyl alcohol mixture. In practice, the apparatus shown in the figure for condensation of the methanol-water mixture can be designed so as to constitute both condensation and distillation in one unit, so that water is withdrawn as a liquid at temperature below 100° C., and methanol is obtained as a vapor which is condensed at temperatures below 65° C., and the $H_2$ and $CO_2$ excess gas returned to the reactor bed as described previously.

While the invention has been described in connection with what is presently considered to be the most practical and preferred embodiments, the invention is not limited to the disclosed embodiment but, on the contrary, is intended to cover various modifications and equivalents included within the spirit and scope of the following claims.

We claim:

1. A method for the joint i) abatement of emission of a "greenhouse" gas by removing carbon dioxide from a water vapor-bearing effluent and ii) manufacture of methanol by reaction of hydrogen with the removed carbon dioxide, comprising:
    a) reacting carbon dioxide in a water vapor-bearing waste gas stream from one of burning fossil fuel, conducting a fermentation process, conducting municipal waste treatment process and operating a lime kiln by flowing contact of the water vapor-bearing waste gas stream with a bed of basic metal oxide at a temperature and pressure suitable to form a metal carbonate,
    b) terminating said contact when said bed has been substantially converted to said carbonate,
    c) heating said carbonate to a temperature and pressure suitable to release carbon dioxide therefrom, and
    d) mixing said released carbon dioxide with hydrogen from a source of hydrogen and passing the resulting mixture over a catalyst of another metal oxide at a suitable temperature and pressure for a reaction to form methanol, and thereby forming methanol.

2. The method of claim 1 wherein the temperature of step a) is from about 330° C. to about 380° C.

3. The method of claim 1 wherein the pressure of step a) is atmospheric.

4. The method of claim 1 wherein the temperature of step c) is from about 475° C. to about 550° C.

5. The method of claim 1 wherein the pressure of step c) is atmospheric.

6. The method of claim 1 wherein the temperature of step d) is from about 140° C. to about 310° C.

7. The method of claim 1 wherein the pressure of step d) is from about 5 to about 55 atmospheres.

8. The method of claim 1 where the source of hydrogen in step d) is from a radiation-augmented electrolytic production process.

9. The method of claim 1 wherein a plurality of beds of metal oxide are provided for alternating use in step a) and at least one of said beds is used to react with carbon dioxide as in step a) to form carbonate while the another said bed which has previously been used in steps a) and b) is being heated in step c) to release carbon dioxide.

10. The method of claim 1 wherein the temperature of step a) is from about 350° C. to about 375° C. the pressure of step a) is atmospheric, the temperature of step c) is from about 500° C. to about 540° C., the pressure of step c) is atmospheric, the temperature of step d) is from about 150° C. to about 300° C., and the pressure of step d) is from about 20 to about 50 atmospheres.

11. The method of claim 1 wherein the metal oxide of step a) is selected from the group consisting of magnesium oxide, zinc oxide, cadmium oxide, and mixtures thereof.

12. The method of claim 1 wherein the metal oxide of step c) is a catalyst selected from the group consisting of ZnO on $ZrO_2$, CuO on ZnO, $CuO/ZnO/Al_2O_3$ and mixtures thereof.

13. The method of claim 1 wherein the process of step d) is conducted so as to also produce hydrocarbons.

* * * * *